United States Patent
Colardelle Da Luz Mano et al.

(10) Patent No.: US 11,883,562 B2
(45) Date of Patent: Jan. 30, 2024

(54) HYDROGELS BASED ON BLOOD PLASMA COMPONENTS, PROCESS AND USES THEREOF

(71) Applicant: UNIVERSIDADE DE AVEIRO, Aveiro (PT)

(72) Inventors: João Filipe Colardelle Da Luz Mano, Aveiro (PT); Catarina De Almeida Custódio, Aveiro (PT); Sara Catarina Nunes Da Silva Santos, Fornos CPV (PT)

(73) Assignee: UNIVERSIDADE DE AVEIRO, Aveiro (PT)

( * ) Notice: Subject to any disclaimer, the term of this patent is extended or adjusted under 35 U.S.C. 154(b) by 570 days.

(21) Appl. No.: 16/955,522

(22) PCT Filed: Dec. 18, 2018

(86) PCT No.: PCT/IB2018/060266
§ 371 (c)(1),
(2) Date: Jun. 18, 2020

(87) PCT Pub. No.: WO2019/123259
PCT Pub. Date: Jun. 27, 2019

(65) Prior Publication Data
US 2020/0316261 A1 Oct. 8, 2020

(30) Foreign Application Priority Data
Dec. 18, 2017 (PT) .......................................... 110463

(51) Int. Cl.
*A61L 27/52* (2006.01)
*A61L 27/10* (2006.01)
*A61L 27/12* (2006.01)
*A61L 27/26* (2006.01)
*A61L 27/36* (2006.01)
*A61L 27/38* (2006.01)
*A61L 27/56* (2006.01)
*C12M 1/12* (2006.01)

(52) U.S. Cl.
CPC ............... *A61L 27/52* (2013.01); *A61L 27/10* (2013.01); *A61L 27/12* (2013.01); *A61L 27/26* (2013.01); *A61L 27/3616* (2013.01); *A61L 27/3834* (2013.01); *A61L 27/56* (2013.01); *C12M 25/00* (2013.01); *A61L 2300/414* (2013.01); *A61L 2400/06* (2013.01)

(58) Field of Classification Search
CPC .......... A61K 8/042; A61K 8/64; A61K 35/12; C08L 101/14; C08L 33/26
See application file for complete search history.

(56) References Cited

U.S. PATENT DOCUMENTS

| 2004/0161444 | A1* | 8/2004 | Song | ....................... A61L 27/46 424/423 |
| 2012/0134968 | A1* | 5/2012 | Wang | ....................... A61L 27/38 435/243 |
| 2014/0335195 | A1* | 11/2014 | Houze | ....................... A61K 8/44 435/374 |

FOREIGN PATENT DOCUMENTS

| EP | 2591812 A1 | 5/2013 |
| WO | WO 2014/035721 A1 | 3/2014 |

OTHER PUBLICATIONS

Zucker (Touro College and University System, Spring 2011, vol. 4, pp. 23-29) (Year: 2011).*
Fass et al (Chemical reviews, 2018, vol. 118, pp. 1169-1198) (Year: 2018).*
Samateh et al (Scientific reports, 2018, vol. 8, pp. 1-8) (Year: 2018).*
Almany et al (Biomaterials, 2005, vol. 26, pp. 2467-2477) (Year: 2005).*
Tae et al (Biomacromolecules, 2007, vol. 8, pp. 1979-1986) (Year: 2007).*
Engelberg (Circulation, 1961, vol. XXIII, pp. 578-581) (Year: 1961).*
Sumida et al (Cell and Tissue Research, 1992, vol. 268, pp. 41-49) (Year: 1992).*
Catarina A. Custódio et al., Photo-Cross-Linked Laminarin-Based Hydrogels for Biomedical Applications, in: Biomacromolecules, 2016, 17 (5), pp. 1602-1609.
Scott A Sell et al., The incorporation and controlled release of platelet-rich plasma-derived biomolecules from polymeric tissue engineering scaffolds, in: Polymer International 61 (12), pp. 1703-1709, Sep. 25, 2012.
Abrams, G. et al, "Platelet-rich Plasma for Articular Cartilage Repair," Sports Med Arthrosc Rev, vol. 21, No. 4, Dec. 4, 2013, pp. 213-219.
Marx, R., "Platelet-Rich Plasma: Evidence to Support Its Use," J Oral Maxillofac Surg, vol. 62, p. 489-496, 2004.
Bieback, K. "Platelet Lysate as Replacement for Fetal Bovine Serum in Mesenchymal Stromal Cell Cultures," Transfusion Medicine and Hemotherapy, Transfus Med Hemother, vol. 40, p. 326-335, 2013.
Carter, M. et al., "Use of Platelet Rich Plasma Gel on Wound Healing: A Systematic Review and Meta-Analysis," Journal of Plastic Surgery, Sep. 15, 2011, p. 382-410.

(Continued)

*Primary Examiner* — Mark V Stevens
(74) *Attorney, Agent, or Firm* — Leason Ellis LLP

(57) ABSTRACT

The present disclosure relates to bioactive hydrogels derived from human blood plasma. More particularly, the disclosure relates to multifunctional materials for cell encapsulation, cell culture platforms, medical treatment apparatus and methods, more particularly, hydrogels derived from human blood components and technologies for use of such materials in research, biomedical treatment, biotech and pharmaceutical industry. The disclosure further relates to 3D printable scaffolds, sponges, foams, fibers, particles, capsules, membranes and injectable systems comprising said hydrogel. Additionally, this disclosure allows for the controlled placement of biologically active components that may be delivered by the hydrogel compositions.

15 Claims, 10 Drawing Sheets

(56) References Cited

OTHER PUBLICATIONS

Peppas, N., "Hydrogels in Biology and Medicine: Form Molecular Principles to Bionanotechnology," Advanced MAterials, vol. 18, p. 1345-1360, 2006.
Eastment, C. et al, "Platelet Lysate Preparations Contain Mitogenic Activity for an Established Rat Mammary Tumor Cell Line," In Vitro Cell Dev B, 1977, 13, 166-166.
Chen et al., "Fundamentals of double network hydrogels." J Mater Chem B. May 14, 2015;3(18):3654-3676.

* cited by examiner

HYDROGELS BASED ON BLOOD PLASMA COMPONENTS, PROCESS AND USES THEREOF

CROSS-REFERENCE TO RELATED APPLICATIONS

This application is a U.S. National Stage Application under 35 U.S.C. § 371 of International Patent Application No. PCT/IB2018/060266, filed Dec. 18, 2018, which claims priority to Portugal Patent Application No. 110463, filed Dec. 18, 2017, the contents of which are each hereby incorporated by reference in their respective entireties.

TECHNICAL FIELD

The present disclosure relates to bioactive hydrogels derived from human blood plasma. More particularly, the disclosure relates to multifunctional materials for cell encapsulation, cell culture platforms, medical treatment apparatus and methods, more particularly, hydrogels derived from human blood components and technologies for use of such materials in research, biomedical treatment, biotech and pharmaceutical industry. The disclosure further relates to 3D printable scaffolds, sponges, foams, fibers, particles, capsules, membranes and injectable systems comprising said hydrogel. Additionally, this disclosure allows for the controlled placement of biologically active components that may be delivered by the hydrogel compositions.

BACKGROUND

Hydrogel compounds have been used in several biomedical fields, including tissue regeneration, drug delivery systems, stem cell delivery systems, cell growth platforms and coating systems. Currently, implantable systems for biomedical applications built into synthetic and natural biodegradable materials are a major research focus. However, at present there are various major concerns in implantable systems uses, such as immunogenicity, biological safety, biocompatibility, degradation rate, and mechanical stability. There is a continuing need to develop new compositions capable of forming in situ biocompatible hydrogel structures that offer improved therapeutic outcomes. Platelets were primarily known to be associated with the hematopoietic system, until 1974, when it was found that the addition of platelets and calcium or the extract from the platelets derived upon activation, to the serum, increased the mitogenic activity and proliferation of cells. [2] [3] This led to a breakthrough in platelet research and led to the interest in this material as cell culture supplement and as injectable system for tissue healing, namely bone and cartilage. [4]

The platelet rich plasma (PRP) is defined as a portion of the plasma fraction of autologous blood having a platelet concentration above baseline. PRP also has been referred to as platelet-enriched plasma, platelet-rich concentrate, autologous platelet gel, and platelet releasate. Platelet releasates have been used to treat wounds since 1985. Direct injection with PRP and platelet lysates (PL) has been attempted to promote cartilage growth and bone healing. [4] Also, PRP can be gelatinized to result in a sort of hydrogel. [5] This type of hydrogels has been explored alone or combined with other materials in tissue regeneration strategies. However, such gels are easy to shrink suffer from high biodegradation and poor mechanical properties. Alternative routes to improve robustness of PRP-based hydrogels is thus desired.

These facts are disclosed in order to illustrate the technical problem addressed by the present disclosure.

GENERAL DESCRIPTION

The present disclosure relates to hydrogel-based materials comprising a polymeric matrix containing blood plasma components, namely platelet rich plasma (PRP) and/or platelet lysates (PL) which are bioactive and have tunable mechanical properties. Tunable mechanical properties are defined as adjustable stiffness, Young's modulus, brittleness, viscoelasticity, and plasticity.

More particularly, the present disclosure relates to the modification of blood plasma derived materials with a chemical agent, in particular methacrylates, ethacrylates, thiols, acrylamides, aldehydes, azides, amine reactive groups or cyclic oligosaccharides or combinations thereof, that allows further chemical or physical crosslinking to create a hydrogel for use in biomedical, biotech and pharmaceutical applications. The present disclosure relates to a novel process for making a crosslinked blood plasma derived hydrogel, which shows increased stability compared to platelet based and fibrin-based hydrogels and sealants of the art. The hydrogels produced by the methods of the present disclosure provide the necessary structural and biochemical support for cell growth and are preferably three dimensional, and particularly suitable for cell culture and drug/cell delivery.

The present disclosure generally relates to hydrogel-based materials composed of a polymeric matrix containing PRP and/or PL which have tunable mechanical properties. More particularly, the present disclosure relates to the modification of plasma derived materials with a chemical agent that allows further chemical or physical crosslinking to create a hydrogel for use in biomedical, biotech and pharmaceutical applications.

The present disclosure distinguishes itself from the prior art because the hydrogels from the prior art may have a human-plasma derived element; however, said element is linked to a polymerizable moiety via polyethylene glycol (PEG). In contrast, the hydrogels now disclosed have a human-plasma derived element directly linked to the polymerizable moiety without any intermediate compound such as PEG. Furthermore, the hydrogel now disclosed has also the advantage that said hydrogel is polymerized in less time than the hydrogels of the prior art, namely the hydrogel now disclosed is polymerized in 30-60 seconds. Moreover, this hydrogel also has better mechanical properties than the hydrogels of the prior art, namely it has better mechanical properties than the hydrogels made of fibrin.

According to the present disclosure PRP and PL may be modified to enhance its chemical reactivity towards a range of reactive monomers. This includes photoreactive precursors prepared by chemical conjugation with acrylate groups. The photoreactive material polymerizes upon ultraviolet (UV) light exposure. The present disclosure also comprises a crosslinkable biodegradable hydrogel that includes PL and PRP precursors and a plurality of physiologically degradable ester linkages, amide linkages, azide-alkyne cycloaddition linkages, acrylate-thiol linkages, urethane linkages, and/or methacrylate-thiol linkages and combinations thereof.

The mechanical properties of PL-based hydrogels, in particular PL-based hydrogels, formed in this process are expected to be superior as compared to conventionally prepared PL-based hydrogels and the properties may easily be tuned to fit the intended purpose. Additionally, the hydrogel according to the present disclosure is also more stable towards enzymatic degradation as compared to the PL state of the art hydrogels. The biological response such as cell function, tissue ingrowth, tissue regeneration and restoration of functions may also be tailored using the hydrogel according to the present disclosure by altering for example the composition, crosslinking chemistry and crosslinking density.

The hydrogel according to the present disclosure may find application as a multifunctional and customizable substrate for cell and tissue growth, coating of cell culture dishes. Currently, there are available on the market few platforms for cell culture and organ development. Matrigel™, HyStem™ and Qgel™ are the mostly used. Matrigel is the only natural based source of proteins and growth factors. Still it has immunogenic potential, as it is derived from mouse sarcoma cells. Compared with using hydrogels, this method is advantageous in creating bioactive hydrogels without complicated synthesis for bioconjugation; and no risk of cross reactivity, immune reaction or disease transmission.

The present disclosure discloses a hydrogel comprising any plasma derived materials, for example PRP or PL and any plasma derived protein.

The present disclosure provides for a composition comprising plasma derived components functionalized by at least one polymerizable moiety. The polymerizable moiety may be selected, for example, from methacrylates, ethacrylates, thiols, acrylamides, aldehydes, azides, amine reactive groups or cyclic oligosaccharides and combinations thereof. As used herein, hydrogel precursor is defined as the chemically modified PL/PRP/plasma derived protein in the form of powder used to prepare hydrogels.

The present disclosure relates to a hydrogel of chemically crosslinked blood plasma components network comprising at least one component of plasma provided with said functional groups, plasma-based hydrogels formed via guest-host complex, plasma-based hydrogels crosslinked enzymatically using appropriate crosslinking agents, such as transglutaminase and combinations thereof.

The present disclosure also relates to a bioactive gel for culture and encapsulation of living cells.

The present disclosure also relates to 3D printable hydrogels and injectable systems comprising the hydrogel according to the present invention and cells.

The present disclosure also relates to the use of the hydrogel according to the present disclosure in lab-on-a-chip systems, microscopy and microarray substrates, cell and tissue culture dishes, microwell plates, microfluidic or sampling and microparticles.

Platelet-rich plasma (PRP) is defined as an increased concentration of autologous platelets, plasma proteins, growth factors and other signaling molecules suspended in a small amount of plasma after centrifugation. It has a greater concentration of bioactive molecules than whole blood and has been used as a tissue injection in a variety of disciplines, including dentistry, orthopedic surgery, and sports medicine.

Platelet lysate (PL) is defined as the platelets content obtained after platelet lysis. Freeze/thaw cycles causes the platelets to lyse, releasing a large quantity of growth factors capable to mediate cell growth and tissue repair.

Plasma derived protein is defined as any protein that can be obtained from plasma or plasma components.

The present disclosure relates to a method for preparation of a hydrogel comprising plasma derived components (PRP or PL) functionalized by at least one polymerizable moiety, which may be selected, from methacrylates, acrylates, thiols, acrylamides, aldehydes, azides, amine reactive groups or cyclic oligosaccharides and combinations thereof.

The present disclosure also relates to a hydrogel composition which may further comprising any plasma derivative protein, for example selected from any protein or growth factor obtained from blood plasma that include but are not limited to serum albumin, fibrinogen, angiotensinogen, vitronectin, apolipoprotein A, complement factors, immunoglobulins, serotransferrin, keratin.

In an embodiment, said hydrogel is formed via chemical crosslinking, guest-host complex, or crosslinked enzymatically using appropriate crosslinking agents, such as transglutaminase and combinations thereof.

In an embodiment, the PL derivate proteins and growth factors retain an activity of mediating cell growth and differentiation.

In an embodiment, the PL derivate proteins and growth factors retain an activity of mediating tissue regeneration following in vivo administration.

In an embodiment, the hydrogel precursor is photo-crosslinkable under aqueous conditions at any temperature, preferably at room or physiological temperature. The hydrogel precursor may be selected from the following list: PRP, PL, or any plasma derivative protein, that include but are not limited to, albumin, fibrinogen, immunoglobulin, serotransferrin or keratin previously conjugated with photo-responsive functional organic groups.

In an embodiment, the hydrogel precursor may further comprise a photoinitiator, in particular a free-radical photoinitiator that include but are not limited to, acetophenone; anisoin; anthraquinone; anthraquinone-2-sulfonic acid, sodium salt monohydrate; (benzene) tricarbonylchromium; 4-(boc-aminomethyl)phenyl isothiocyanate; benzin; benzoin; benzoin ethyl ether; benzoin isobutyl ether; benzoin methyl ether; benzoic acid; benzophenyl-hydroxycyclohexyl phenyl ketone; 3,3',4,4'-benzophenonetetracarboxylic dianhydride; 4-benzoylbiphenyl; 2-benzyl-2-(dimethylamino)-4'-morpholinobutyrophenone; 4,4'-bis(diethylamino)benzophenone; 4,4'-bis(dimethylamino)benzophenone; Michler's ketone; camphorquinone; 2-chlorothioxanthen-9-one; 5-dibenzosuberenone; (cumene) cyclopentadienyliron(II) hexafluorophosphate; dibenzosuberenone; 2,2-diethoxyacetophenone; 4,4'-dihydroxybenzophenone; 2,2-dimethoxy2-phenylacetophenone; 4-(dimethylamino)benzophenone; 4,4'-dimethylbenzyl; 2,5-dimethylbenzophenone; 3,4-dimethylbenzophenone; diphenyl(2,4,6-trimethylbenzoyl)phosphine oxide; 2-hydroxy-2-methylpropiophenone; 4'-ethoxyacetophenone; 2-ethylanthraquinone; ferrocene; 3'-hydroxyacetophenone; 4'-hydroxyacetophenone; 3-hydroxybenzophenone; 4-hydroxybenzophenone; 1-hydroxycyclohexyl phenyl ketone; 2-hydroxy-2-methylpropiophenone; 2-methylbenzophenone; 3-methyl benzophenone; methybenzoylformate; 2-methyl-4'-(methylthio)-2-morpholinopropiophenone; 9,10-phenanthrenequinone; 4'-phenoxyacetophenone; thioxanthen-9-one; triarylsulfonium hexafluoroantimonate salts; triarylsulfonium hexafluorophosphate salts; 3-mercapto-1-propanol; 11-mercapto-1-undecanol; 1-mercapto-2-propanol; 3-mercapto-2-butanol; hydrogen peroxide; benzoyl peroxide; 4,4'-dimethoxybenzoin; 2,2-dimethoxy-2-phenylacetophenone; dibenzoyl disulphides; diphenyldithiocarbonate; 2,2'-azobisisobutyronitrile (AIBN); camphorquinone (CQ); eosin; dimethylaminobenzoate (DMAB); dimethoxy-2-phenyl-acetophenone (DMPA); Quanta-cure ITX photosensitizes (Biddle Sawyer); Irgacure 907 (Ciba Geigy); Irgacure 2959 (CIBA Geigy); Irgacure 651 (Ciba Geigy); Darocur 2959 (Ciba Geigy); ethyl-4-N,N-dimethylaminobenzoate (4EDMAB); 1-[-(4-benzoylphenylsulfanyl)phenyl]-2-methyl-2-(4-methylphenylsulfonyl)propan1-one; 1-hydroxy-cyclohexyl-phenyl-ketone.

In general, photoinitiators are utilized at concentrations ranging between approximately 0.005% w/v and 5.0% w/v. For example, photoinitiators can be utilized at concentrations of about 0.005% w/v, about 0.01% w/v, about 0.025% w/v, about 0.05% w/v, about 0.075% w/v, about 0.1% w/w, about 0.125% w/v, about 0.25% w/v, about 0.5% w/v, about 0.75% w/v, about 1% w/v, about 1.125% w/v, about 1.25% w/v, about 1.5% w/v, about 1.75% w/v, about 2% w/v, about 2.125% w/v, about 2.25% w/v, about 2.5% w/v, about 2.75% w/v, about 3% w/v, about 3.125% w/v, about 3.25% w/v, about 3.5% w/v, about 3.75% w/v, about 4% w/v, about 4.125% w/v, about 4.25% w/v, about 4.5% w/v, about 4.75% w/v, about 5% w/v or higher, although high concentrations of photoinitiators can be toxic to cells.

In an embodiment, the hydrogel may be for use as a biomaterial, in particular it may be used as a biomaterial in medicine, pharmaceutical studies, biotechnological processes, ex vivo and in vitro studies.

Any amount of modified PL or PRP or proteins can be present in the hydrogel, provided that it is sufficient to form a hydrogel having functional characteristics described herein. For example, depending on the amount of chemical modification, the hydrogel can comprise PL or PRP or proteins in the amount of about 5% (w/v) to about 95% (w/v). In some embodiments, the hydrogel can comprise modified PL or PRP or proteins in an amount of about 5% (w/v) to about 75% (w/v), about 10% (w/v) to about 50% (w/v), about 15% (w/v) to about 40% (w/v) or about 20% (w/v) to about 30% (w/v). In some embodiments, the hydrogel can comprise modified PL or PRP or proteins in the amount of about 5% (w/v), about 6% (w/v), about 7% (w/v), about 8% (w/v), about 9% (w/v), about 10% (w/v), about 11% (w/v), about 12% (w/v), about 13% (w/v), about 14% (w/v), about 15% (w/v).

In an embodiment, the hydrogel material may further comprise another natural or synthetic based polymer, such as chitosan, gelatin, collagen, alginate, laminarin, hyaluronic acid or polyethylene glycol (PEG).

In an embodiment, the hydrogel may further be combined with another hydrogel, forming a double-network or an inter-penetrating network, such as chitosan, gelatin, alginate, laminarin, hyaluronic acid, poly(vinyl alcohol), polyacrylamide, carboxymethylcellulose, sodium starch glycolate, sodium carboxymethyl starch, dextran, dextran sulfate, xanthan, gellan, pectinic acid, deoxyribonucleic acids, ribonucleic acid, albumin, polyacrolein potassium, sodium glycine carbonate, poly(acrylic acid) and its salts, polyacrylonitrile, poly(styrene sulfonate), poly(aspartic acid), polylysine, polyvinylpyrrolidone, polyvinyl alcohol, CARBOPOL, ultramylopectin, poly(ethylene glycol), neutral cellulose derivatives, microcrystalline cellulose, powdered cellulose, cellulose fibers, and starch.

In an embodiment, the hydrogel material further comprises inorganic materials such as calcium phosphate or magnetic particles or bioglass particles or fibers.

In an embodiment, the hydrogel may further comprise a biological active agent or a therapeutic agent, in particular wherein the biological active agent is a cell, a stem cell, a protein, a therapeutic agent, a biomolecule, diagnostic marker and probe or mixture thereof.

In an embodiment, hydrogel material may be in the form of 3D printable scaffolds, sponges, foams, fibers, particles, capsules, membranes.

The present disclosure relates to a hydrogel comprising:
a human plasma-derived element selected from human platelet rich plasma, human platelet lysate, human plasma protein, or combinations thereof;
wherein the human plasma-derived element is directly linked to at least one polymerizable moiety selected from a methacrylate, acrylate, ethacrylate, thiol, acrylamide, aldehyde, azide, amine reactive group, cyclic oligosaccharides, or combinations thereof.

In an embodiment, the hydrogel may further comprise a biocompatible polymer, wherein the biocompatible polymer comprises at least one polymerizable moiety selected from a methacrylate, acrylate, ethacrylate, thiol, acrylamide, aldehyde, azide, amine reactive group, cyclic oligosaccharides, or combinations thereof.

In an embodiment, the hydrogel may further comprise a biocompatible polymer selected from: chitosan, alginate, gelatin, collagen, laminarin, hyaluronic acid, polyethylene glycol, or combinations thereof, preferable said biocompatible polymer comprises the polymerize moiety selected from a methacrylate, acrylate, ethacrylate, thiol, acrylamide, aldehyde, azide, amine reactive group, cyclic oligosaccharides, or combinations thereof.

In an embodiment, the hydrogel may further comprise a biocompatible polymer selected from: chitosan, alginate, gelatin, collagen, laminarin, hyaluronic acid, polyethylene glycol, or combinations thereof, wherein the polymer is linked to the human plasma-derived element or it is mixed with the human plasma-derived element.

In an embodiment, the hydrogel may further comprise a biocompatible polymer selected from: chitosan, alginate, gelatin, collagen, laminarin, hyaluronic acid, polyethylene glycol, or combinations thereof, wherein the polymer is cross-linked with the plasma-derived element.

In an embodiment, the human plasma-derived element may have a concentration of 5-90% $w_{human\ plasma-derived\ element}/V_{hydrogel}$, preferably 10-50% $w_{human\ plasma-derived\ element}/V_{hydrogel}$, more preferably 15-30% $w_{human\ plasma-derived\ element}/V_{hydrogel}$.

In an embodiment, the human platelet rich plasma has a concentration of 5-90% $w_{human\ platelet\ rich\ plasma}/V_{hydrogel}$, preferably 10-50% $w_{human\ platelet\ rich\ plasma}/V_{hydrogel}$, more preferably 15-30% $w_{human\ platelet\ rich\ plasma}/V_{hydrogel}$.

In an embodiment, the human platelet lysate may have a concentration of 5-90% $w_{human\ platelet\ lysate}/V_{hydrogel}$, preferably 10-50% $w_{human\ platelet\ lysate}/V_{hydrogel}$, more preferably 10-30% $w_{human\ platelet\ lysate}/V_{hydrogel}$, even more preferably 10-15% $w_{human\ platelet\ lysate}/V_{hydrogel}$.

In an embodiment, the human plasma protein may have a concentration of 5-90% $w_{human\ plasma\ protein}/V_{hydrogel}$, preferably 10-50% $w_{human\ plasma\ protein}/V_{hydrogel}$, more preferably 15-30% w human plasma protein/$V_{hydrogel}$.

In an embodiment, the human plasma-derived element may have a degree of substitution between 10%-90%, preferably 14-70%, more preferably 20-60%, even more preferably 25-60% wherein the degree of substitution stands for the ratio of modified peptides per number of total peptides in the plasma-derived element.

In an embodiment, the human plasma protein may be selected from serum albumin, fibrinogen, angiotensinogen, vitronectin, apolipoprotein A, complement factors, immunoglobulins, serotransferrin, keratin, or combinations thereof.

In an embodiment, the hydrogel may further comprises a growth factor, in particular the growth factor may be selected from the following list: platelet-derived growth factor (PDGF), transforming growth factor (TGF), platelet factor interleukin (IL), platelet-derived angiogenesis factor (PDAF), vascular endothelial growth factor (VEGF), epidermal growth factor (EGF), insulin-like growth factor IGF, fibroblast growth factor (FGF).

In an embodiment, the hydrogel may further comprise inorganic materials selected from: calcium phosphate, magnetic particles, bioglass particles, fibers, or combinations thereof.

In an embodiment, the hydrogel may further comprise a biological agent selected from a cell, a stem cell, a protein, a therapeutic agent, a biomolecule, a diagnostic marker, a probe, or combinations thereof.

In an embodiment, the hydrogel may be ross-linked via chemical crosslinking, guest-host complexes, or crosslinked enzymatically via transglutaminase, or combinations thereof.

In an embodiment, the hydrogel now disclosed may comprise 10-15% $w_{human\ platelet\ lysate}/V_{hydrogel}$ wherein the human platelet lysate is directly linked to at least one polymerizable moiety selected from a methacrylate; and wherein the degree of substitution is between 14-25%, preferably wherein the degree of methacrylation is between 14-25%.

In an embodiment, the hydrogel may be in the form of a foam, sponge, particle, capsule, fiber, membrane, disc, in particular it may be lyophilized.

In an embodiment, the foam, sponge, particle, capsule, fiber, membrane, or disc when lyophilized may have a 5-100% $w_{human\ plasma-derived\ element}/V_{hydrogel}$, preferably 10-50% $w_{human\ plasma-derived\ element}/V_{hydrogel}$.

In an embodiment, the foam, sponge, particle, capsule, fiber, membrane, or disc may have a 5-100% $w_{human\ platelet\ rich\ plasma}/V_{hydrogel}$, preferably 10-50% $w_{human\ platelet\ rich\ plasma}/V_{hydrogel}$.

In an embodiment, the foam, sponge, particle, capsule, fiber, membrane, or disc may have a 5-100% $w_{human\ platelet\ lysate}/V_{hydrogel}$, preferably 10-50% $w_{human\ platelet\ lysate}/V_{hydrogel}$.

In an embodiment, the foam, sponge, particle, capsule, fiber, membrane, or disc may have a 5-100% $w_{human\ plasma\ protein}/V_{hydrogel}$, preferably 10-50% w $w_{human\ plasma\ protein}/V_{hydrogel}$.

In an embodiment, hydrogel may further be combined with a second hydrogel, forming a double-network or an inter-penetrating network, in particular the second hydrogel is selected from: chitosan, gelatin, alginate, laminarin, hyaluronic acid, poly(vinyl alcohol), polyacrylamide, carboxymethylcellulose, sodium starch glycolate, sodium carboxymethyl starch, dextran, dextran sulfate, xanthan, gellan, pectinic acid, deoxyribonucleic acids, ribonucleic acid, albumin, polyacrolein potassium, sodium glycine carbonate, poly(acrylic acid) and its salts, polyacrylonitrile, poly(styrene sulfonate), poly(aspartic acid), polylysine, polyvinylpyrrolidone, polyvinyl alcohol, CARBOPOL, ultramylopectin, poly(ethylene glycol), neutral cellulose derivatives, microcrystalline cellulose, powdered cellulose, cellulose fibers, or starch.

The present disclosure also relates to a hydrogel for use in medicine.

In an embodiment, the hydrogel may be for use in cell culture, drug delivery, cell delivery, organ development, tissue growth, tissue engineering.

This disclosure also relates to a method for preparing a hydrogel according to any of the previous claims, comprising the step of: linking a human plasma-derived element selected from human platelet rich plasma, human platelet lysate, human plasma derived protein, or combinations thereof, to at least one polymerizable moiety selected from a methacrylate, acrylate, ethacrylate, thiol, acrylamide, aldehyde, azide, amine reactive group, cyclic oligosaccharides, or combinations thereof.

BRIEF DESCRIPTION OF THE DRAWINGS

The following figures provide preferred embodiments for illustrating the description and should not be seen as limiting the scope of disclosure.

DETAILED DESCRIPTION

The present disclosure provides tunable crosslinked blood plasma derived hydrogel, their processing method and use in tissue regeneration, drug delivery, organ development, cell culture and tissue growth.

Figure 1:
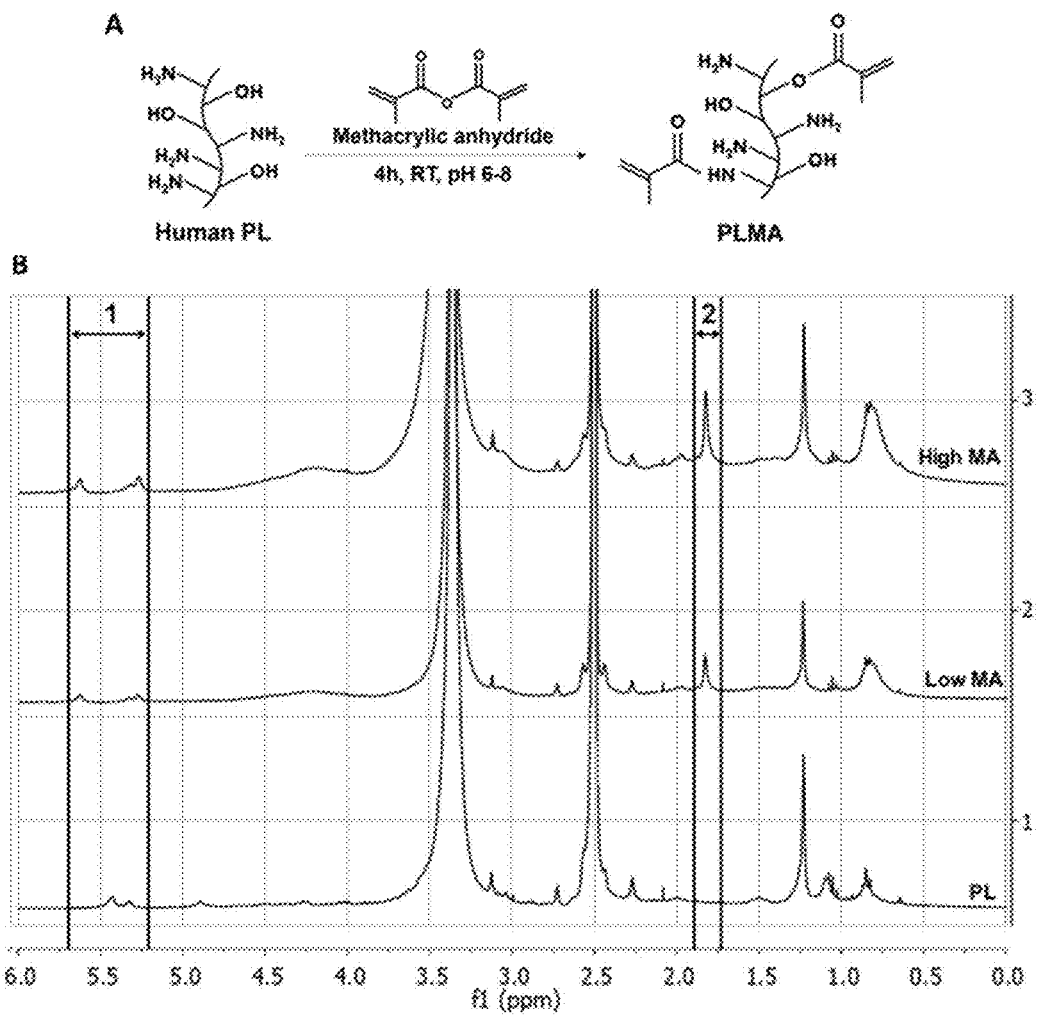
FIG. 1: A) Possible route for the reaction of a protein/peptide with methacrylic anhydride. B) $^1$H-NMR spectra for PL, PL with a degree of substitution, in particular a degree of methacrylation, of 14% (low modification) and PL with a degree of substitution, in particular a degree of methacrylation, of 25% (high modification) with distinctive peaks characteristics of methacrylate groups: double bound methacrylate (1) and —$CH_3$ of methacrylate group (2).

Different functional groups in proteins from PL and PRP are sensitive to chemical modifications as shown in FIG. 1A. In particular, the reactive functional groups existing in proteins are located on the side groups of amino acid residues, including hydroxyl groups (from serine, threonine, hydroxyproline, and hydroxylysine residues), amino groups (from lysine and hydroxylysine residues), and carboxylic acid substitutes (from aspartic acid and glutamic acid residues). In particular, methacryloyl substitution occurs rapidly and with high yield with reactive functional groups present in all proteins. Addition of acryloyl groups to the amine/hydroxyl/carboxylic acid-containing side groups of proteins present in PL was used to make it light polymerizable. PL were converted to a photo-polymerizable material through the reaction with methacrylic anhydride at controlled pH, in particular at pH=8 and temperature, in particular at 18-25° C.

In an embodiment, the use of different ratios PL:methacrylic anhydride, which stands for methacrylation degree, allows for tailoring the physicochemical and biological properties of the hydrogels for specific applications. The properties of the material can also be controlled with irradiation time and concentration of photo reactive PL hydrogel precursor. These will allow obtaining hydrogels possessing a wide range of physical properties, e.g., strength, stiffness, toughness, durability, degradability, mass transport and water uptake, according to the desired use. A ratio PL:methacrylic anhydride between $10:1 \times 10^{-3}$ (v/v)-10:5 (v/v) is suitable for the preparation of precursors for hydrogels.

In an embodiment, different degrees of methacrylation were obtained by varying the molar ratio of methacrylic anhydride to PL concentration, in particular the following degrees of methacrylation were obtained 14% (low modification) and 25% (high modification).

In an embodiment, the insertion of acrylate groups in the PL was verified by proton nuclear magnetic resonance ($^1$H-NMR) spectroscopy performed before and after modification. Methacrylation was confirmed by the peaks at 1.8-2.0, 5.7-5.9, 6.1-6.3 ppm from methacrylate group (FIG. 1B).

Figure 2:
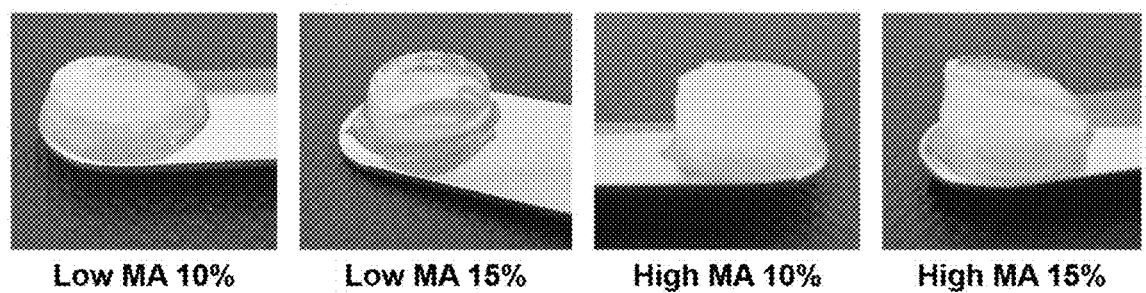
FIG. 2: Plasma derived hydrogels formed from PL with a degree of substitution, in particular a degree of methacrylation, of 14% (low modification) and PL with a degree of substitution, in particular a degree of methacrylation, of 25% (high modification), at 10% (w/v) and 15% (w/v).
Figure 7:
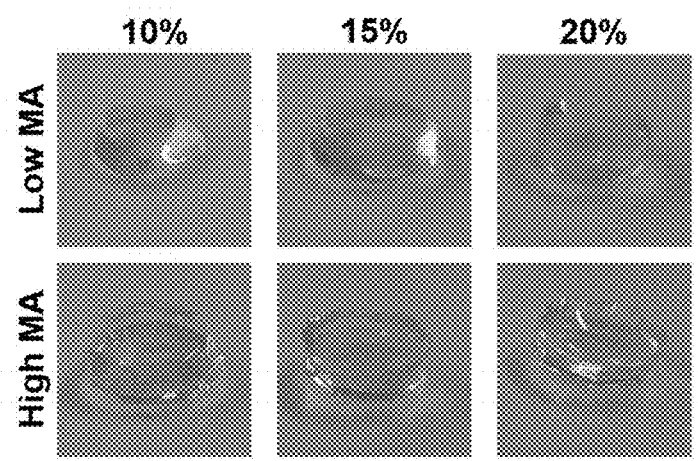
FIG. 7: Plasma derived hydrogels formed from PL with a degree of substitution, in particular a degree of methacrylation, of 14% (low modification) and PL with a degree of substitution, in particular a degree of methacrylation, of 25% (high modification), at 10% (w/v), 15% (w/v) and 20% (w/v).

In an embodiment, the polymer is crosslinked by UV light in the presence of a photo-initiator (2-Hydroxy-4'-(2-hydroxyethoxy)-2-methylpropiophenone) at mild temperatures (FIGS. 2 and 7).

In an embodiment, to determine the effect of methacrylation degree, hydrogel precursor concentration and irradiation time on the mechanical properties of the PL hydrogels, compression assays were performed on samples with methacrylation degrees of 14% (low modification) and 25% (high modification) and concentrations of 10 $w_{plaquet\ lysate}/v_{hydrogel}$% and 15 $w/v_{hydrogel}$% and irradiation time of 30 s and 60 s.

Figure 3:
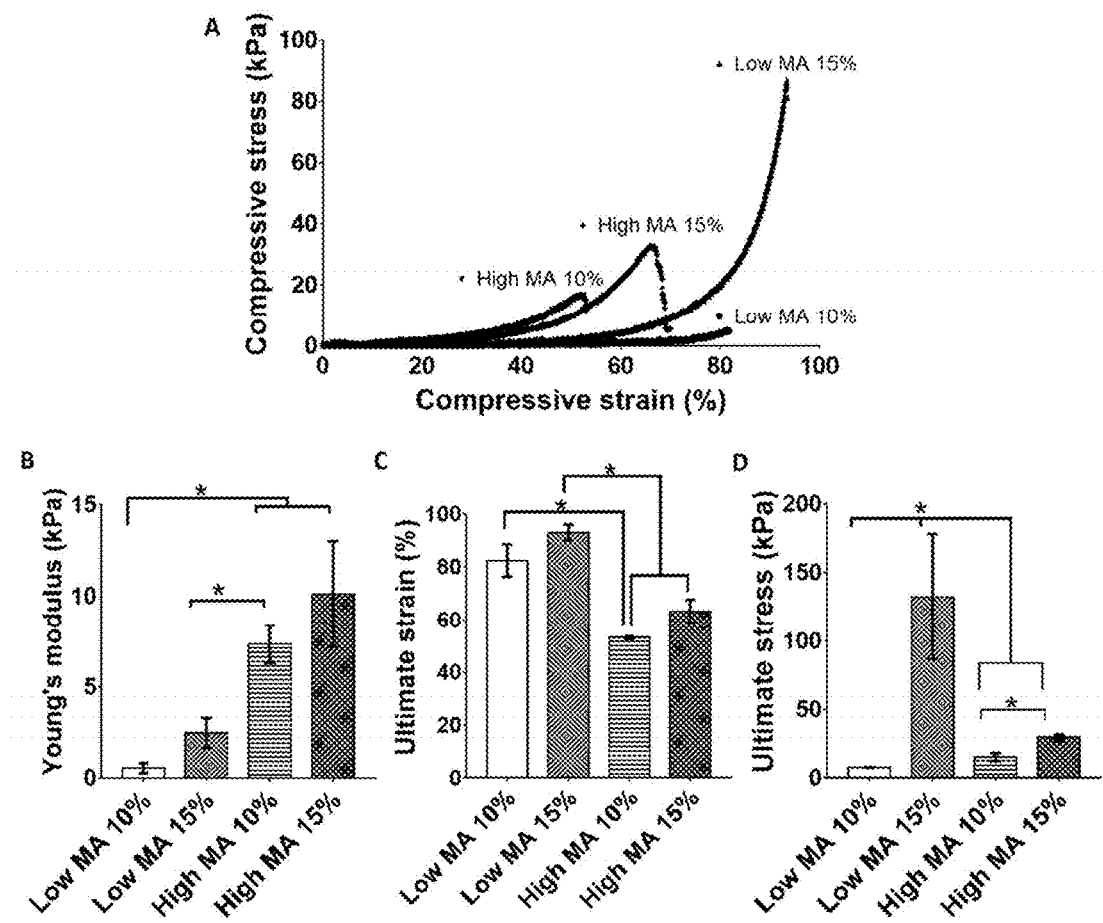
FIG. 3: A) Representative compressive stress-strain curves for PL with a degree of substitution, in particular a degree of methacrylation, of 14% (low modification) and PL with a degree of substitution, in particular a degree of methacrylation, of 25% (high modification) hydrogels at 10% (w/v) and 15% (w/v), B) Young's modulus, C) ultimate strain and D) ultimate stress. Statistical analysis through unpaired t test showed significant differences (*$p<0.05$) between the analyzed groups.
Figure 8A:
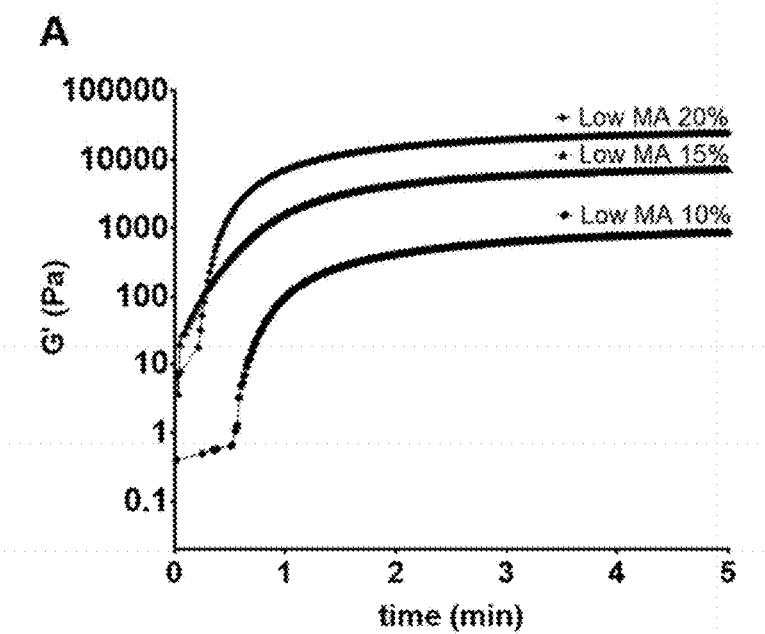
FIG. 8: A) Representative curves for storage modulus (G') for PL with a degree of substitution, in particular a degree of methacrylation, of 14% (low modification) hydrogels at 10% (w/v), 15% (w/v) and 20% (w/v). (B) Representative curves for storage modulus (G') for PL with a degree of substitution, in particular a degree of methacrylation, of 25% (high modification) hydrogels at 10% (w/v), 15% (w/v) and 20% (w/v). (C) t½ and tan δ for PL with a degree of substitution, in particular a degree of methacrylation, of 14% (low modification) hydrogels at 10% (w/v), 15% (w/v) and 20% (w/v) and for PL with a degree of substitution, in particular a degree of methacrylation, of 25% (high modification) hydrogels at 10% (w/v), 15% (w/v) and 20% (w/v). Statistical analysis through two-tailed unpaired t test showed significant differences (*p<0.01) between the analyzed groups.
Figure 8B:
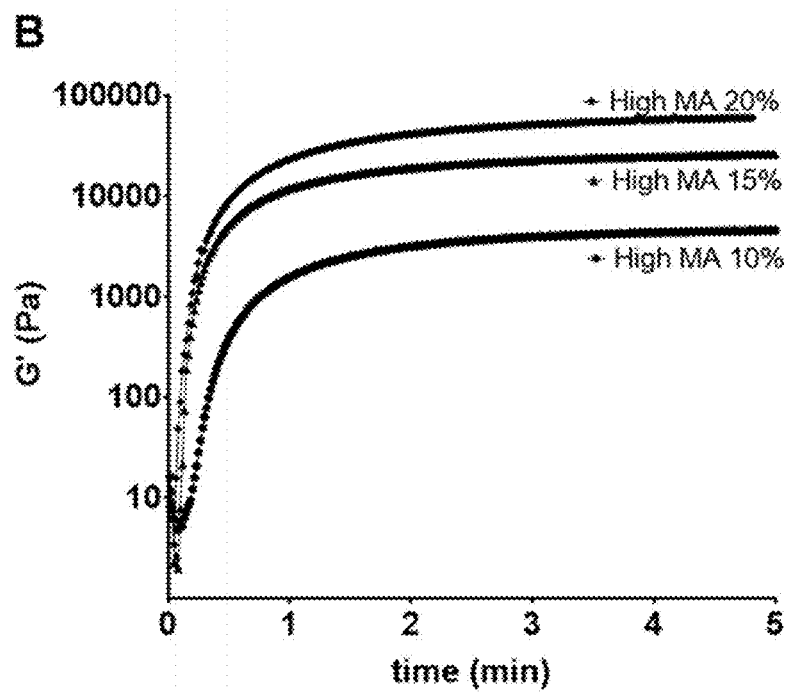
Figure 8C:
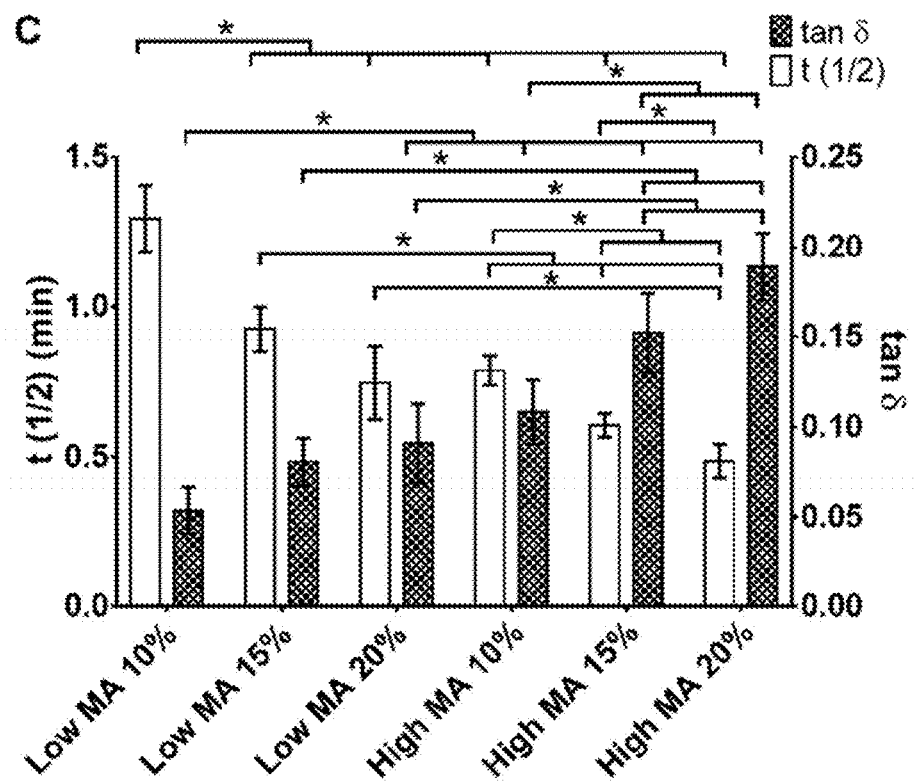
Figure 9:
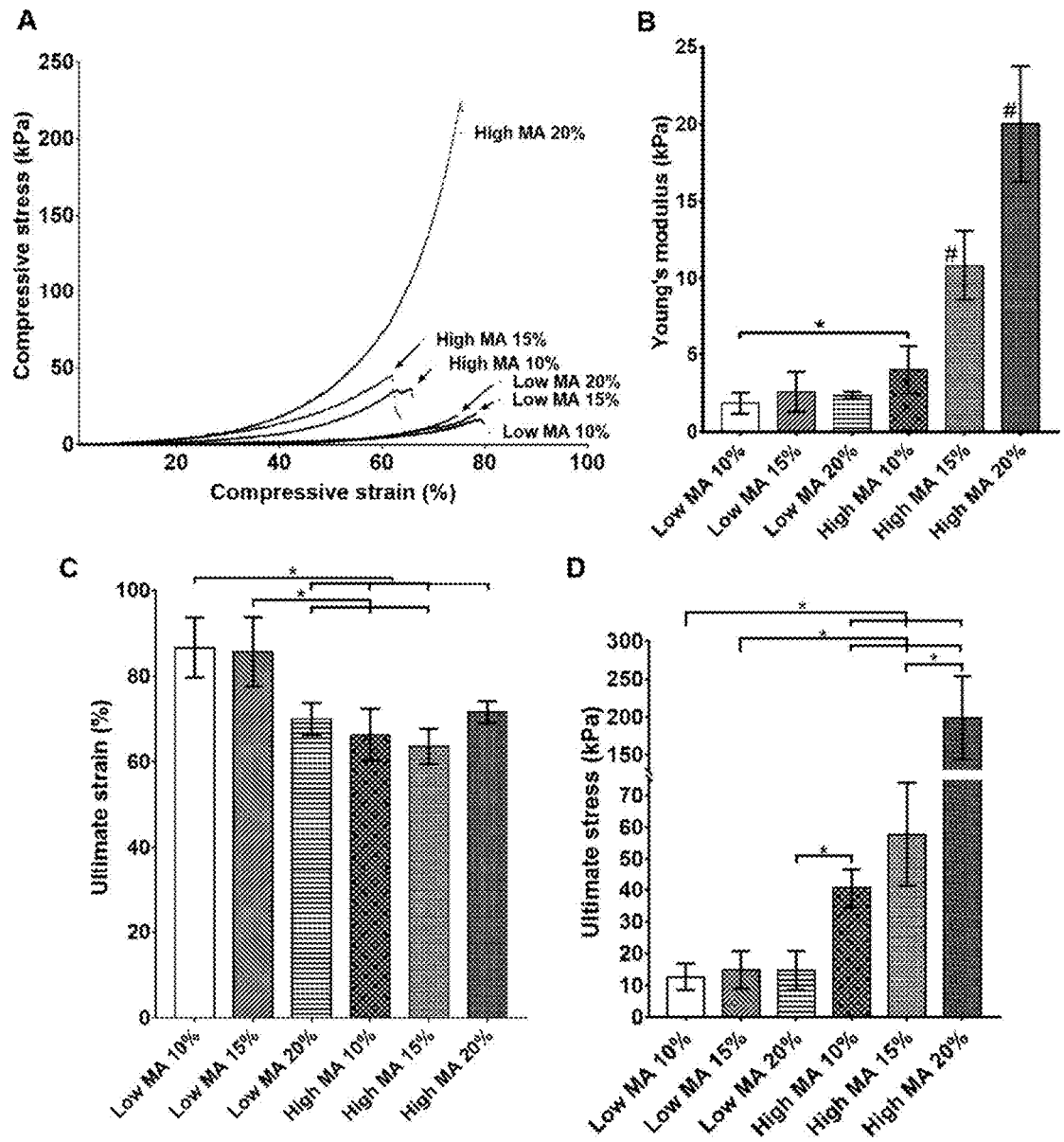
FIG. 9: A) Representative compressive stress-strain curves for PL with a degree of substitution, in particular a degree of methacrylation, of 14% (low modification) and PL with a degree of substitution, in particular a degree of methacrylation, of 25% (high modification) hydrogels at 10% (w/v), 15% (w/v) and 20% (w/v), B) Young's modulus, C) ultimate strain and D) ultimate stress. Statistical analysis through two-tailed unpaired t test showed significant differences (*p<0.01) between the analyzed groups.

In general, increasing the degree of methacrylation increased the stiffness at all strain levels (FIGS. 3, 8 and 9). Similarly, maintaining a constant degree of methacrylation while increasing the PL concentration significantly increased the stiffness under all conditions tested. Apparently, the increase of irradiation time from 30 s to 60 s do not change the mechanical properties of the hydrogels.

The degree of methacrylation is defined as the degree of methacryloyl substitution on the proteins from platelet lysates or platelet rich plasma.

The degree of methacrylation may be determined using the following method or methods: $^1$H NMR, mass spectroscopy, fluoraldehyde assay, Habeeb method.

In an embodiment, structural analysis by scanning electronic microscopy (SEM) was performed. Platelet hydrogels have a porous network influenced by precursor concentration as showed in FIGS. 4A, 4B, 10A and 10B. For lower (10% w/v) precursor concentration, hydrogels have larger porous than in higher (15% w/v or 20% w/v) PLMA concentrations.

Figure 4A:
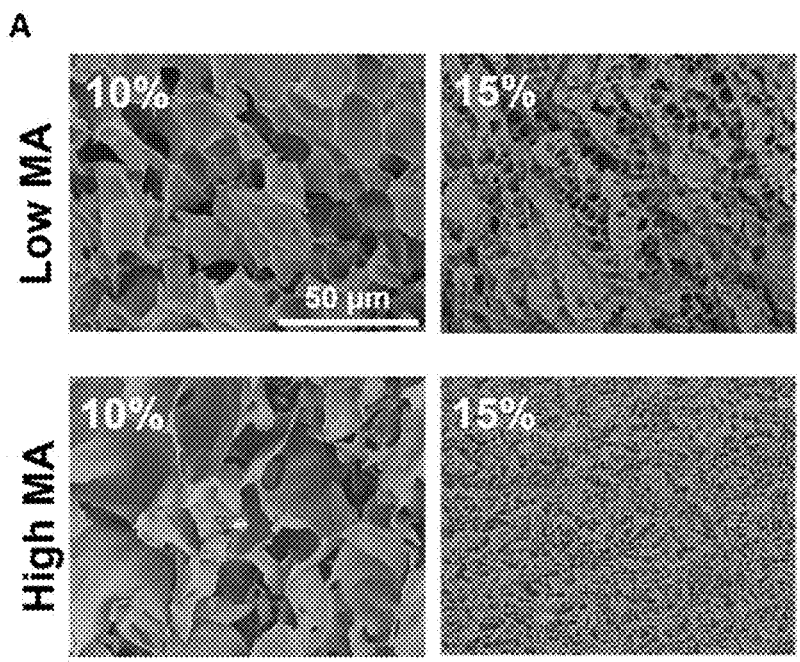
FIG. 4: A) Representative cross-section SEM images of PL with a degree of substitution, in particular a degree of methacrylation, of 14% (low modification) and PL with a degree of substitution, in particular a degree of methacrylation, of 25% (high modification) hydrogels at 10% (w/v) and 15% (w/v). B) Pore size values obtained for PL with a degree of substitution, in particular a degree of methacrylation, of 14% (low modification) and PL with a degree of substitution, in particular a degree of methacrylation, of 25% (high modification) at 10% (w/v) and 15% (w/v) hydrogels. C) Swelling ratio for PL with a degree of substitution, in particular a degree of methacrylation, of 14% (low modification) and PL with a degree of substitution, in particular a degree of methacrylation, of 25% (high modification) hydrogels at 10% (w/v) and 15% (w/v). Statistical analysis through unpaired t test showed significant differences (*$p<0.05$) between the analyzed groups.
Figures 4B, 4C:
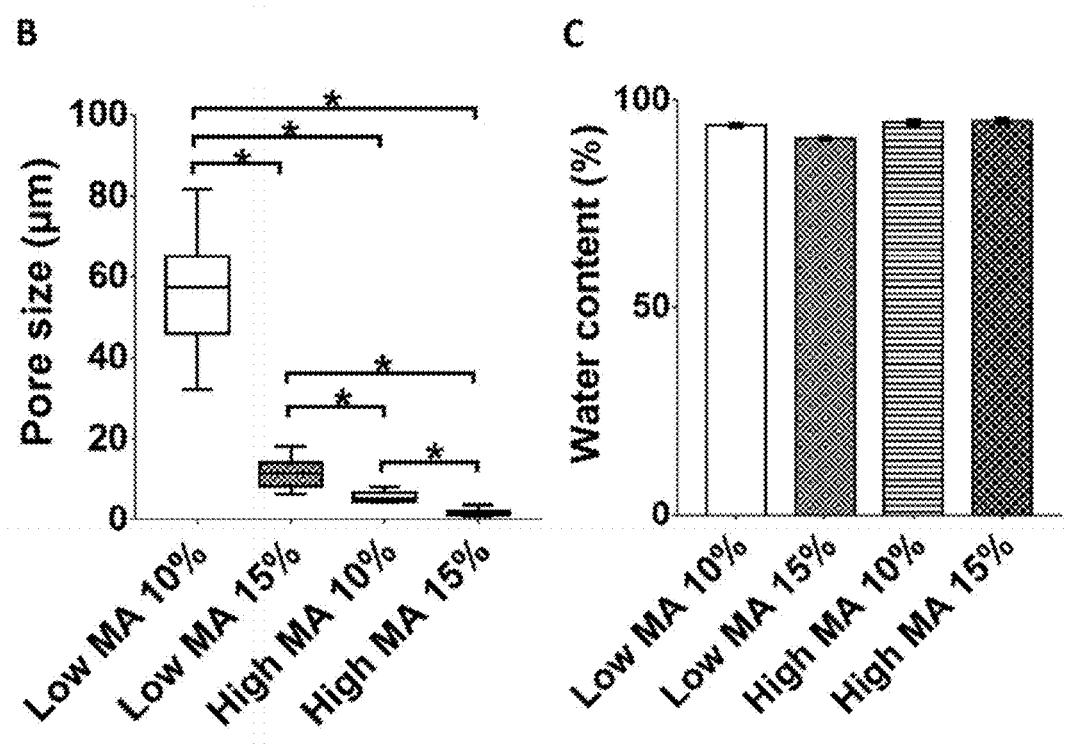
Figure 10:
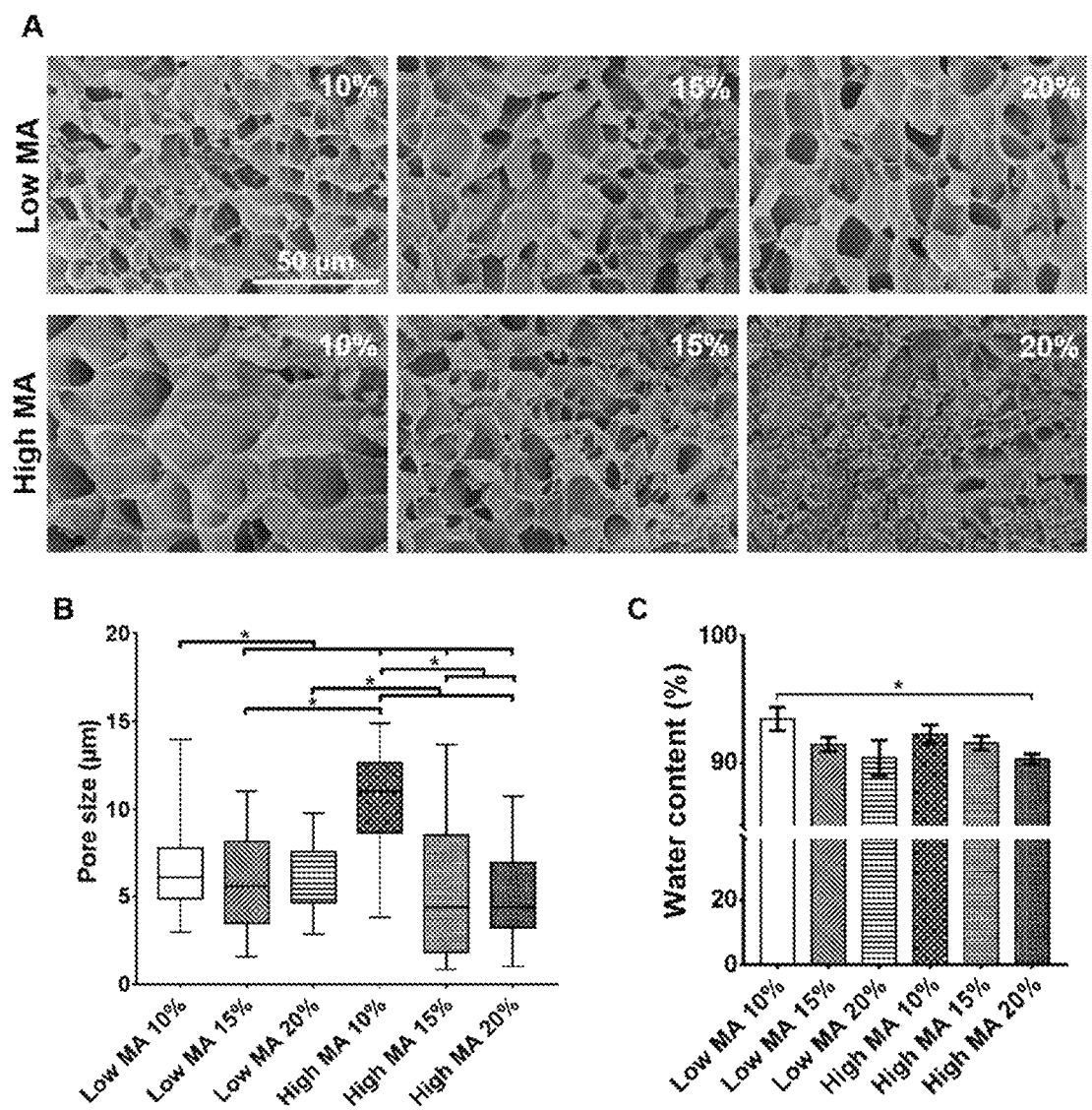
FIG. 10: A) Representative cross-section SEM images of PL with a degree of substitution, in particular a degree of methacrylation, of 14% (low modification) and PL with a degree of substitution, in particular a degree of methacrylation, of 25% (high modification) hydrogels at 10% (w/v), 15% (w/v) and 20% (w/v). B) Pore size values obtained for PL with a degree of substitution, in particular a degree of methacrylation, of 14% (low modification) and PL with a degree of substitution, in particular a degree of methacrylation, of 25% (high modification) at 10% (w/v), 15% (w/v) and 20% (w/v) hydrogels. C) Swelling ratio for PL with a degree of substitution, in particular a degree of methacrylation, of 14% (low modification) and PL with a degree of substitution, in particular a degree of methacrylation, of 25% (high modification) hydrogels at 10% (w/v), 15% (w/v) and 20% (w/v). Statistical analysis through two-tailed unpaired t test showed significant differences (*p<0.01) between the analyzed groups.

The water content of hydrogels was also evaluated. Results shown that this parameter is not significantly different between all the studied conditions. In general, plasma-based hydrogels have 90% of water content (FIGS. 4C and 10C).

Figure 5:
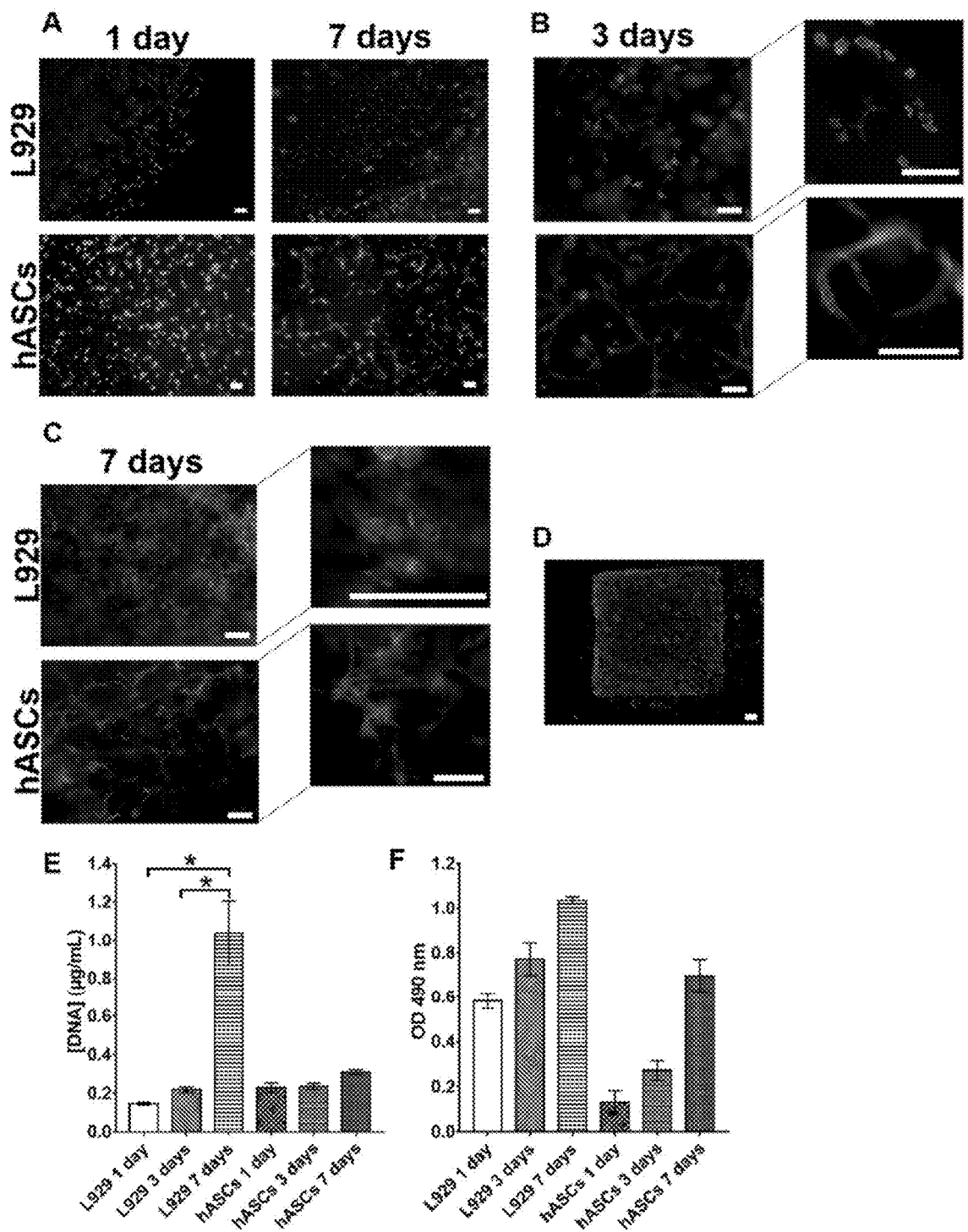
FIG. 5: Representative fluorescence images for: A) L929 and hASCs live/dead at 1 and 7 days of culture. B and C) L929 and hASCs DAPI/Phalloidin staining at 3 and 7 days of cell culture. (D) DAPI/Phalloidin staining for hydrogel microstructures of encapsulated L929 at 7 days of culture. DNA (E) and MTS (F) results for L929 and hASCs at 1 day, 3 and 7 days of cell culture. Statistical analysis through unpaired t test showed significant differences (*$p<0.05$) between the analyzed groups. L929 cells were encapsulated in PL with a degree of substitution, in particular a degree of methacrylation, of 14% (low modification) (10% w/v). hASCs cells were encapsulated in PL with a degree of substitution, in particular a degree of methacrylation, of 14% (low modification) (15% w/v).
Figure 6:
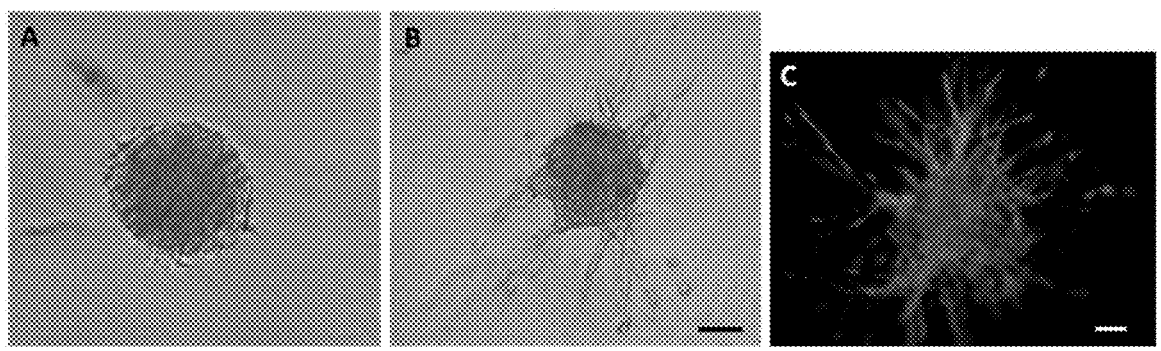
FIG. 6: MG-63 spheroids embedded into Matrigel (A) and embedded into PL gels (B). C) Live-dead imaging of a MG-63 spheroid on PL gel.
Figure 11:
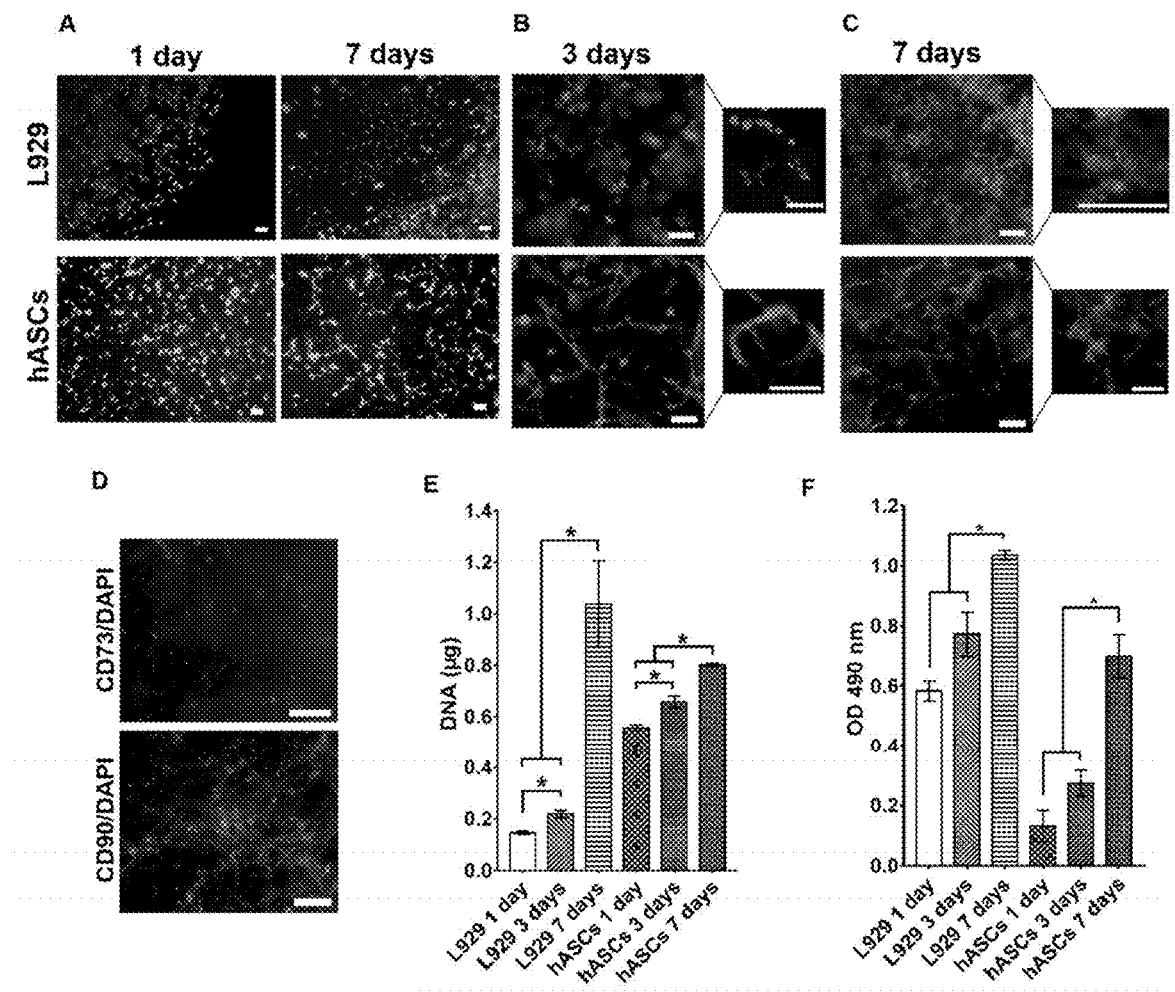
FIG. 11: Representative fluorescence images for: A) L929 and hASCs live/dead at 1 and 7 days of culture. B and C) L929 and hASCs DAPI/Phalloidin staining at 3 and 7 days of cell culture. (D)Immunocytochemistry images of hASCs with CD90/DAPI and CD73/DAPI at 7 days of cell culture. DNA (E) and MTS (F) results for L929 and hASCs at 1 day, 3 and 7 days of cell culture. Statistical analysis through two-tailed unpaired t test showed significant differences (*p<0.01) between the analyzed groups. L929 cells were encapsulated in PL with a degree of substitution, in particular a degree of methacrylation, of 14% (low modification) (10% w/v). hASCs cells were encapsulated in PL with a degree of substitution, in particular a degree of methacrylation, of 14% (low modification) (15% w/v). Scale bar: 100 μm.

In an embodiment, in vitro cytotoxicity/viability and proliferation screening was performed. The ability of the hydrogels of the present disclosure to sustain cells viability was assessed using L929 cells and human adipose derived stem cells (hASCs). The gels with encapsulated cells were then exposed to UV light to allow photo-polymerization. Afterwards, the discs were incubated for different time periods in cell culture medium. Cell viability after specific times of culturing (24 h and 7 days) was assessed using Calcein AM staining. Cell viability assay showed a uniform distribution of viable cells in the photo-crosslinked gels (FIGS. 5A and 11A). Cell proliferation and morphology on the gels was also evaluated. After specific time points the gels were fixed and the cells stained with dapi/phalloidin. An increasing density of live cells was observed which demonstrate that these hydrogels supports cells proliferation (FIGS. 5B, 5C, 5D, 11B, 11C, 11E and 11F).

Following cell encapsulation, cells on a solution of the material of the invention may be injected into the patient at the site of injury or defect and gellified in situ. In another application, the material of this invention may be used as a bioink to incorporate in bioprinters or similar apparatus to obtain hydrogels with controlled structure, or prepare hydrogels that find applications as supporting platforms for ex-vivo and in vitro biological studies, hydrogels and microgels for cell encapsulation and cell expansion for pharmaceutical studies (e.g. drug screening) or biotechnological (e.g. production of proteins) applications.

With several advantages, the autologous material now disclosed provides the basis for the development of a new autologous minimally-invasive system that could be used alone or seeded with cells suitable for restoring, maintaining or enhancing tissue/organ function. The hydrogels now disclosed are non-immunogenic, biodegradable under physiological conditions due to hydrolysable bonds in the polymer backbone, resulting in non-toxic fragments that are easily removed, from the body. Heterogeneous approaches can also be envisaged for the use of the proposed materials for ex-vivo and in vitro applications.

This novel hydrogel opens up new possibilities for drug discovery and development as it can be used for the generation of disease specific models for different tissue disorders. PRP/PL/plasma derived protein hydrogel precursor could be generated from patient-specific blood plasma. In addition, this could be combined with patient-specific cells.

The hydrogel now disclosed may be used as a 3D platform for spheroid invasion assessment.

Figure 12:
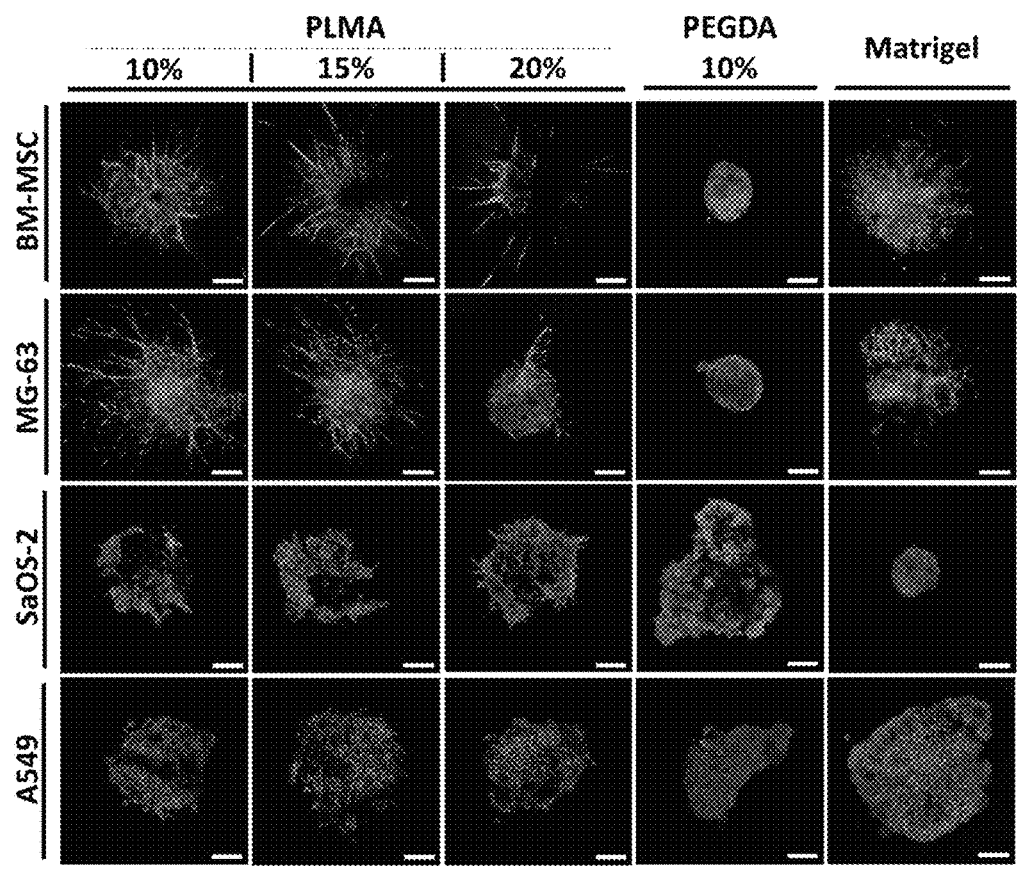
FIG. 12: Representative fluorescence images of DAPI/Phalloidin staining of BM-MSC, MG-63, SaOS-2 and A549 spheroids embedded into PL with a degree of substitution, in particular a degree of methacrylation, of 14% (low modification) hydrogels at 10% (w/v), 15% (w/v) and 20% (w/v), embedded into PEGDA hydrogel (10% (w/v)) and embedded into Matrigel® at 14 days of culture.
Figure 13:
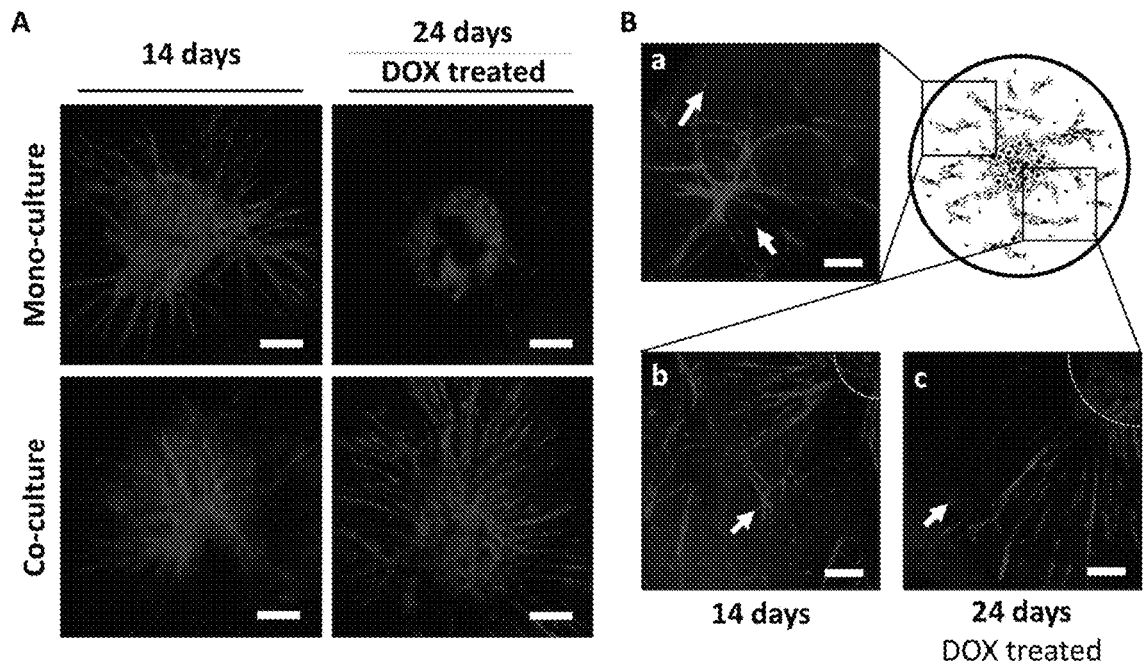
FIG. 13: A) Fluorescence microscopy images of DAPI/Phalloidin staining of the established 3D mono- and co-culture models at 14 days of culture and after a doxorubicin (DOX) treatment (24 days of culture). (B) Schematics representation of the established 3D co-culture OS model and fluorescence microscopy images of DAPI/Phalloidin staining demonstrating the cellular network formed by hBM-MSC and MG-63 tumor cells at (a, b) 14 days of culture and (c) 24 days of culture, after drug treatment.

In an embodiment, BM-MSCs, MG-63, SaOS-2 and A549 spheroids were embedded into Matrigel, embedded into PEGDA gels and embedded into PL gels. Tumor spheroid growth and invasion was improved when using PL derived gels (FIG. 12).

This novel hydrogel may be used for 3D in vitro model for disease development that: is physiologically relevant and/or patient-derived and meets the requirements of the pharmaceutical industry (HTS format, easy to manipulate, cost effective, reproducible and robust).

In an embodiment, MG-63 spheroids, BM-MSCs and osteoblasts were co-cultured to recapitulate tumor cell-microenvironment interaction of an invading tumor. PL hydrogels were able to support an invasive tumor morphology and produce an in vivo-like drug response (FIG. 12).

The synthesized PL derived material may be processed in the form of hydrogels, microfibers, particles, capsules, foams, sponges films or membranes with dimensions ranging from nanoscale to microscale. It can be also used as a coating substrate for cell culture and tissuegrowth.

The term "comprising" whenever used in this document is intended to indicate the presence of stated features, integers, steps, components, but not to preclude the presence or addition of one or more other features, integers, steps, components or groups thereof.

It will be appreciated by those of ordinary skill in the art that unless otherwise indicated herein, the particular sequence of steps described is illustrative only and can be varied without departing from the disclosure. Thus, unless otherwise stated the steps described are so unordered meaning that, when possible, the steps can be performed in any convenient or desirable order.

The disclosure should not be seen in any way restricted to the embodiments described and a person with ordinary skill in the art will foresee many possibilities to modifications thereof.

The above described embodiments are combinable.

The following claims further set out particular embodiments of the disclosure.

REFERENCES

[1] N. A. Peppas, J. Z. Hilt, A. Khademhosseini, R. Langer, *Adv Mater* 2006, 18, 1345-1360.

[2] C. T. Eastment, D. A. Sirbasku, *In Vitro Cell Dev B* 1977, 13, 166-166.

[3] K. Bieback, *Transfus Med Hemoth* 2013, 40, 326-335.

[4] G. D. Abrams, R. M. Frank, L. A. Fortier, B. J. Cole, *Sports Med Arthrosc* 2013, 21, 213-219. *J Oral Maxil Surg* 2004, 62, 489-496.

[5] M. J. Carter, C. P. Fylling, L. K. Parnell, *Eplasty* 2011, 11, e38.

The invention claimed is:

1. A hydrogel, comprising
a human platelet lysate,
wherein the human platelet lysate is modified to be directly linked to at least one polymerizable moiety, wherein the at least one polymerizable moiety is a methacrylate;
wherein the human platelet lysate has a concentration of 10-20% $w_{human\ platelet\ lysate}/V_{hydrogel}$; and
wherein the degree of substitution ranges between 14-25% of modified peptides per number of total peptides in the human platelet lysate.

2. The hydrogel according to claim 1, further comprising a biocompatible polymer, wherein the biocompatible polymer comprises at least one polymerizable moiety selected from the group consisting of: a methacrylate, acrylate, ethacrylate, thiol, acrylamide, aldehyde, azide, amine reactive group, cyclic oligosaccharides, and combinations thereof.

3. The hydrogel according to claim 2, wherein the biocompatible polymer is selected from the group consisting of: chitosan, alginate, gelatin, collagen, laminarin, hyaluronic acid, polyethylene glycol, and combinations thereof.

4. The hydrogel according to claim 3, wherein the biocompatible polymer is linked to the human platelet lysate or is mixed with the human platelet lysate.

5. The hydrogel according to claim 3, wherein the biocompatible polymer is cross-linked with the human platelet lysate.

6. The hydrogel according to claim 1, wherein the hydrogel further comprises a growth factor.

7. The hydrogel according to claim 6, wherein the growth factor is selected from the group consisting of: platelet-derived growth factor (PDGF), transforming growth factor (TGF), platelet factor interleukin (IL), platelet-derived angiogenesis factor (PDAF), vascular endothelial growth factor (VEGF), epidermal growth factor (EGF), insulin-like growth factor IGF, and fibroblast growth factor (FGF).

8. The hydrogel according to claim 1, wherein the hydrogel further comprises inorganic materials selected from the group consisting of: calcium phosphate, magnetic particles, bioglass particles, inorganic fibers, and combinations thereof.

9. The hydrogel according to claim 1, further comprising a biological agent selected from the group consisting of: a cell, a stem cell, a protein, a therapeutic agent, a biomolecule, a diagnostic marker, a probe, and combinations thereof.

10. The hydrogel according to claim 1, wherein the hydrogel is cross-linked via chemical crosslinking, guest-host complexes, or crosslinked enzymatically via transglutaminase, or by combinations thereof.

11. The hydrogel according to claim 1, wherein the hydrogel is in the form of a foam, sponge, particle, capsule, fiber, membrane, or disc.

12. The hydrogel according to claim 11, wherein the foam, sponge, particle, capsule, fiber, membrane, or disc is lyophilized.

13. The hydrogel according to claim 1, wherein said hydrogel is further combined with a second hydrogel, forming a double-network or an inter-penetrating network.

14. The hydrogel according to claim 13, wherein the second hydrogel is selected from the group consisting of: chitosan, gelatin, alginate, laminarin, hyaluronic acid, poly (vinyl alcohol), polyacrylamide, carboxymethylcellulose, sodium starch glycolate, sodium carboxymethyl starch, dextran, dextran sulfate, xanthan, gellan, pectinic acid, deoxyribonucleic acids, ribonucleic acid, albumin, polyacrolein potassium, sodium glycine carbonate, poly(acrylic acid) and its salts, polyacrylonitrile, poly(styrene sulfonate), poly(aspartic acid), polylysine, polyvinylpyrrolidone, ultramylopectin, poly(ethylene glycol), microcrystalline cellulose, powdered cellulose, cellulose fibers, and starch.

15. A method for preparing a hydrogel of the type comprising a human platelet lysate, wherein the human platelet lysate is directly linkable to at least one polymerizable moiety, the method comprising the step of:
directly linking the human platelet lysate to at least one polymerizable moiety, wherein the at least one polymerizable moiety is a methacrylate;
wherein the human platelet lysate has a concentration of 10-15% $w_{human\ platelet\ lysate}/V_{hydrogel}$; and
wherein the degree of substitution ranges between 14-25%.

* * * * *